United States Patent

Yoon

Patent Number: 5,954,733
Date of Patent: Sep. 21, 1999

[54] SUTURING INSTRUMENT WITH ROTATABLY MOUNTED NEEDLE DRIVER AND CATCHER

[76] Inventor: InBae Yoon, 2101 Highland Ridge Dr., Phoenix, Md. 21131

[21] Appl. No.: 09/064,133

[22] Filed: Apr. 22, 1998

Related U.S. Application Data

[63] Continuation of application No. 08/758,648, Nov. 27, 1996, Pat. No. 5,759,188.

[51] Int. Cl.$^6$ .................................................. A61B 17/04
[52] U.S. Cl. ........................................... 606/147; 606/144
[58] Field of Search .................................. 606/139, 144, 606/145, 147, 148

[56] References Cited

U.S. PATENT DOCUMENTS

| | | |
|---|---|---|
| 919,138 | 4/1909 | Drake et al. . |
| 1,037,864 | 9/1912 | Carlson et al. . |
| 1,131,163 | 3/1915 | Saunders et al. . |
| 1,155,378 | 10/1915 | Steedman . |
| 1,449,087 | 3/1923 | Bugbee . |
| 1,822,330 | 9/1931 | Ainslie . |
| 1,916,722 | 7/1933 | Ende . |
| 2,213,830 | 9/1940 | Anastasi . |
| 2,580,964 | 1/1952 | Skaller . |
| 2,601,564 | 6/1952 | Smith . |
| 2,646,045 | 7/1953 | Priestley . |
| 2,959,172 | 11/1960 | Held . |
| 3,090,386 | 5/1963 | Curtis . |
| 3,139,089 | 6/1964 | Schwerin . |
| 3,349,772 | 10/1967 | Rygg . |
| 3,470,875 | 10/1969 | Johnson . |
| 3,842,840 | 10/1974 | Schweizer . |
| 3,946,740 | 3/1976 | Bassett . |
| 4,109,658 | 8/1978 | Hughes . |
| 4,164,225 | 8/1979 | Johnson et al. . |
| 4,257,420 | 3/1981 | Terayama ................................. 128/303 |
| 4,440,171 | 4/1984 | Nomoto et al. . |
| 4,557,265 | 12/1985 | Andersson . |
| 4,621,640 | 11/1986 | Mulhollan et al. . |
| 4,635,638 | 1/1987 | Weintraub et al. . |
| 4,935,027 | 6/1990 | Yoon . |
| 5,037,433 | 8/1991 | Wilk et al. . |
| 5,100,421 | 3/1992 | Christoudias ............................ 606/144 |
| 5,147,373 | 9/1992 | Ferzli . |
| 5,152,769 | 10/1992 | Baber ....................................... 606/145 |
| 5,171,257 | 12/1992 | Ferzli ....................................... 606/205 |
| 5,181,919 | 1/1993 | Bergman et al. . |
| 5,209,741 | 5/1993 | Spaeth . |
| 5,222,508 | 6/1993 | Contarini . |
| 5,224,948 | 7/1993 | Abe et al. ................................. 606/147 |
| 5,234,443 | 8/1993 | Phan et al. . |

(List continued on next page.)

FOREIGN PATENT DOCUMENTS

| | | |
|---|---|---|
| 482881A1 | 4/1992 | European Pat. Off. . |
| 0337579 | 4/1904 | France . |
| 0395073 | 8/1973 | U.S.S.R. . |
| 2260704 | 4/1993 | United Kingdom . |
| WO 97/37583 | 10/1997 | WIPO . |

*Primary Examiner*—Gary Jackson
*Attorney, Agent, or Firm*—Blank Rome Comisky & McCauley LLP

[57] ABSTRACT

An instrument for suturing anatomical tissue with a suture needle includes a handle, a needle driver mounted by the handle for rotation along a first arcuate path having a radius of curvature commensurate with a radius of curvature of the suture needle, and a needle catcher mounted by the handle for rotation along a second arcuate path coplanar with the first arcuate path and having a radius of curvature commensurate with the radius of curvature of the suture needle. The needle driver and the needle catcher each include needle holding members selectively operable to grasp and release the suture needle so that, when the needle holding members of the driver are operated to grasp the suture needle, the driver can be rotated to drive the suture needle through anatomical tissue positioned between the driver and the catcher, and when the needle holding members of the catcher are operated to grasp the suture needle, the needle holding members of the driver can be operated to release the suture needle, thereby allowing the catcher to be rotated to pull the suture material through the anatomical tissue.

21 Claims, 3 Drawing Sheets

U.S. PATENT DOCUMENTS

| | | |
|---|---|---|
| 5,244,945 | 9/1993 | Mulhaupt et al. . |
| 5,211,650 | 5/1993 | Noda . |
| 5,261,917 | 11/1993 | Hasson et al. . |
| 5,281,238 | 1/1994 | Chin et al. . |
| 5,300,082 | 4/1994 | Sharpe et al. ............................ 606/147 |
| 5,304,185 | 4/1994 | Taylor . |
| 5,305,121 | 4/1994 | Moll . |
| 5,308,353 | 5/1994 | Beurrier . |
| 5,320,632 | 6/1994 | Heidmueller . |
| 5,336,230 | 8/1994 | Leichtling et al. . |
| 5,336,231 | 8/1994 | Adair . |
| 5,356,424 | 10/1994 | Buzerak et al. . |
| 5,364,408 | 11/1994 | Gordon . |
| 5,364,409 | 11/1994 | Kuwabara et al. . |
| 5,374,275 | 12/1994 | Bradley et al. . |
| 5,376,096 | 12/1994 | Foster . |
| 5,389,098 | 2/1995 | Tsuruta et al. . |
| 5,389,103 | 2/1995 | Melzer et al. ............................ 606/144 |
| 5,395,367 | 3/1995 | Wilk . |
| 5,397,325 | 3/1995 | Della Badia et al. . |
| 5,403,328 | 4/1995 | Shallman . |
| 5,403,329 | 4/1995 | Hinchcliffe . |
| 5,437,681 | 8/1995 | Meade et al. . |
| 5,454,823 | 10/1995 | Richardson et al. . |
| 5,462,561 | 10/1995 | Voda . |
| 5,462,562 | 10/1995 | Elkus . |
| 5,468,251 | 11/1995 | Buelna . |
| 5,470,338 | 11/1995 | Whitfield et al. ....................... 606/144 |
| 5,474,057 | 12/1995 | Makower et al. . |
| 5,474,568 | 12/1995 | Scott . |
| 5,477,794 | 12/1995 | Klundt . |
| 5,478,344 | 12/1995 | Stone et al. . |
| 5,478,345 | 12/1995 | Stone et al. . |
| 5,480,406 | 1/1996 | Nolan et al. . |
| 5,496,310 | 3/1996 | Exconde et al. . |
| 5,496,334 | 3/1996 | Klundt et al. . |
| 5,503,634 | 4/1996 | Christy . |
| 5,520,703 | 5/1996 | Essig et al. . |
| 5,540,704 | 7/1996 | Gordon et al. . |
| 5,540,705 | 7/1996 | Meade et al. . |
| 5,545,148 | 8/1996 | Wurster . |
| 5,562,640 | 10/1996 | McCabe et al. . |
| 5,562,685 | 10/1996 | Mollenauer et al. . |
| 5,562,686 | 10/1996 | Sauer et al. . |
| 5,562,703 | 10/1996 | Desai . |
| 5,569,164 | 10/1996 | Lurz . |
| 5,569,269 | 10/1996 | Hart et al. . |
| 5,569,270 | 10/1996 | Weng . |
| 5,573,542 | 11/1996 | Stevens . |
| 5,578,048 | 11/1996 | Pasqualucci et al. . |
| 5,582,617 | 12/1996 | Klieman et al. . |
| 5,591,181 | 1/1997 | Stone et al. . |
| 5,601,575 | 2/1997 | Measamer et al. . |
| 5,603,718 | 2/1997 | Xu . |
| 5,607,435 | 3/1997 | Sachdeva et al. . |
| 5,609,601 | 3/1997 | Kolesa et al. . |
| 5,626,588 | 5/1997 | Sauer et al. . |
| 5,632,751 | 5/1997 | Piraka . |
| 5,632,752 | 5/1997 | Buelna . |
| 5,643,292 | 7/1997 | Hart . |
| 5,662,663 | 9/1997 | Shallman . |
| 5,674,230 | 10/1997 | Tovey et al. . |
| 5,702,407 | 12/1997 | Kaji ........................................ 606/139 |
| 5,707,379 | 1/1998 | Fleenor et al. . |
| 5,709,693 | 1/1998 | Taylor . |
| 5,709,694 | 1/1998 | Greenberg et al. . |
| 5,713,908 | 2/1998 | Jameel et al. . |
| 5,722,990 | 3/1998 | Sugarbaker et al. . |
| 5,810,805 | 9/1998 | Sutcu et al. ............................. 606/45 |

SUTURING INSTRUMENT WITH ROTATABLY MOUNTED NEEDLE DRIVER AND CATCHER

RELATED APPLICATION DATA

This application is a continuation of application Ser. No. 08/758,648 filed on Nov. 27, 1996, now U.S. Pat. No. 5,759,188.

BACKGROUND OF THE INVENTION

1. Field of the Invention

The present invention pertains to suturing of bodily or anatomical tissue and, more particularly, to an apparatus and method for suturing anatomical tissue during endoscopic and open surgical procedures.

2. Discussion of the Related Art

Suturing of bodily tissue, that is, the practice of using lengths of suture material to ligate or approximate tissue, is a time consuming part of most surgical procedures including both open surgery and endoscopic or closed surgery. By "open surgery" is meant surgery wherein the surgeon gains access to the surgical site by a relatively large incision and by "endoscopic surgery" is meant minimally invasive surgery wherein the surgeon gains access to the surgical site via one or more portals through which endoscopes are introduced to view the surgical site and through which instruments, such as forceps, cutters, needle holders and the like, are introduced to the surgical site.

In the past, suturing has been accomplished with the use of a sharp suture needle carrying a length of suture material, the suture needle being caused to penetrate and pass through the tissue pulling the suture material through the tissue. Once the suture material has been pulled through the tissue, the surgeon ties a knot in the suture material, the knotting procedure allowing the surgeon to adjust the tension on the suture material to accommodate the particular tissue being sutured and to control approximation, occlusion, attachment or other conditions of the tissue.

The process of tissue penetration and knotting of the suture material can be time consuming and tedious work, particularly when performed in connection with microsurgery and endoscopic surgery and can unduly prolong the duration of surgery and therefore the period in which the patient is under anesthesia. Nevertheless, endoscopic surgery is preferred over open surgery due to the greatly reduced trauma and wound healing time for the patient and due to cost savings associated with shorter hospital stays and performing surgery in non-hospital or out-patient surgery sites. Accordingly, there has been much effort to develop techniques for facilitating the suturing normally performed by use of a suture needle and a length of suture material. Alternative techniques proposed have included electrical coagulation, mechanical devices such as clips, clamps and staples, and lasers; however, no alternative technique has yet been well accepted by surgeons to produce the results obtained by suturing and tying. Thus, there is a great need for suturing techniques useful in endoscopic surgery to permit surgeons to suture anatomical tissue using suture needles and lengths of suture material in a time efficient, consistent and precise manner.

The performance of an endoscopic procedure typically involves creation of one or a number of puncture sites through a wall of an anatomical cavity using a penetrating instrument including an obturator, such as a trocar, disposed within a portal sleeve. After the penetrating instrument has penetrated into the anatomical cavity, the obturator is withdrawn leaving the sleeve in place to form a portal in the cavity wall for the introduction of instruments such as endoscopes, scissors, forceps, needle holders and the like into the anatomical cavity. Suturing is typically performed with a needle holding instrument or holder having a pair of jaws adapted to hold the body of a suture needle. The jaws of the needle holding instrument are inserted through the portal sleeve and are positioned at the operative site by manipulation of a handle at the proximal end of the instrument outside the body. With a suture needle held between the jaws of the needle holding instrument, the handle is manipulated to cause a tip of the needle to be pushed through the tissue being sutured. Once the tip of the suture needle has been pushed through the tissue, the jaws of the needle holding instrument must either be opened to release the suture needle so that the tip of the needle can be grasped and pulled through the tissue therewith, or a second needle holding instrument must be introduced at the operative site through another portal to grasp the tip of the suture needle after it has emerged from the tissue being sutured. The former technique requires further adjustment of the suture needle within the jaws of the needle holder before another stitch can be made; and, while use of a second needle holding instrument for pulling the needle through the anatomical tissue allows the first needle holding instrument to grasp the body of the suture needle in the manner required to make additional stitches, it is generally desirable to minimize the number of puncture sites created for performing a particular endoscopic procedure.

SUMMARY OF THE INVENTION

Accordingly, it is a primary object of the present invention to overcome the above-mentioned disadvantages of the prior art and to improve suturing instruments and methods of suturing anatomical tissue.

Another object of the present invention is to permit suturing of anatomical tissue without the need of having to use multiple needle holding instruments.

Yet another object of the present invention is to minimize the number of puncture sites required for suturing anatomical tissue in an endoscopic procedure by inserting a pair of needle holders through a single puncture site with a suturing instrument having a handle operable to move the needle holders relative to one another in a cooperative manner to suture anatomical tissue.

It is a further object of the present invention to permit a suturing instrument as well as other medical instruments and devices to be introduced through a single portal in an endoscopic procedure without the need of having to withdraw the suturing instrument from the portal.

Some of the advantages of the present invention over the prior art are that suturing of anatomical tissue can be accomplished in a time efficient, consistent and precise manner, that suturing can be accomplished using standard suture needles and filamentous suture materials without the need of having to insert additional instruments at the operative site, that single-handed suturing is made possible, that conventional handle structures can be used to provide users with a familiar feel and to decrease adaptation time, and that the instrument can be made sterilizable for reuse or disposable for single patient use as desired.

The present invention is generally characterized in an instrument for suturing anatomical tissue with a suture needle including a handle, a needle driver mounted by the handle for rotation along a first arcuate path having a radius of curvature commensurate with a radius of curvature of the suture needle, and a needle catcher mounted by the handle for rotation along a second arcuate path coplanar with the first arcuate path and having a radius of curvature commensurate with the radius of curvature of the suture needle. The needle driver and the needle catcher each include needle holding members selectively operable to grasp and release the suture needle so that, when the needle holding members of the driver are operated to grasp the suture needle, the driver can be rotated to drive the suture needle through anatomical tissue positioned between the driver and the catcher, and when the needle holding members of the catcher are operated to grasp the suture needle, the needle holding members of the driver can be operated to release the suture needle, thereby allowing the catcher to be rotated to pull the suture material through the anatomical tissue. In one embodiment, distal ends of the needle driver and the needle catcher are configured to hold a suture needle at an angle relative to the longitudinal axis of the instrument and are longitudinally movable relative to an elongate tubular member between extended positions where the needle driver and the needle catcher bend outwardly away from a longitudinal axis of the elongate tubular member and retracted positions where the needle driver and the needle catcher are forced inwardly toward the longitudinal axis. An inner tubular member may be disposed within the elongate tubular member with a small radial clearance to define an annular space therebetween, with the needle driver and needle catcher being movably disposed within the annular space. If provided, the inner tubular member preferably extends through the handle to define a longitudinal operating passage or channel along the length of the instrument, with a valve and/or a coupling being disposed at a proximal end of the inner tubular member to control passage of fluids and instruments through the channel.

Another aspect of the present invention is generally characterized in a method of suturing anatomical tissue using a length of suture material attached to a curved suture needle with a radius of curvature, the method including the steps of grasping the suture needle with a first needle holder mounted by a handle, positioning the anatomical tissue between a tip of the suture needle and a second needle holder mounted by the handle, rotating the first needle holder in a first direction along an arcuate path having a radius of curvature commensurate with the radius of curvature of the suture needle to cause the tip of the needle to penetrate the anatomical tissue, receiving the tip of the suture needle in the second needle holder, grasping the suture needle with the second needle holder, releasing the suture needle from the first needle holder, and rotating the second needle holder in the first direction along a second arcuate path having a radius of curvature commensurate with the radius of curvature of the suture needle to pull the needle and the suture material through the anatomical tissue.

Yet another aspect of the present invention is generally characterized in method of suturing anatomical tissue using a length of suture material attached to a suture needle including the steps of positioning the suture needle in openings formed through opposed sides of a hook-shaped needle holding member of a needle driver mounted by a handle, grasping the suture needle by moving a cooperating needle holding member of the needle driver distally relative to the hook-like member to contact the suture needle, positioning the anatomical tissue between a tip of the suture needle and a needle catcher mounted by the handle, moving the needle driver toward the needle catcher to cause the tip of the needle to penetrate the anatomical tissue, receiving the tip of the suture needle in openings formed through opposed sides of a hook-shaped needle holding member of the needle catcher, grasping the suture needle by moving a cooperating needle holding member of the needle catcher distally relative to the hook-shaped member, releasing the suture needle from the needle driver by moving the cooperating member proximally relative to the hook-shaped member, and moving the needle catcher away from needle driver to pull the suture needle through the anatomical tissue.

Other objects and advantages of the present invention will become apparent from the following description of the preferred embodiments taken in conjunction with the accompanying drawings, wherein like parts in each of the several figures are identified by the same reference numerals or by reference numerals having the same last two digits.

DESCRIPTION OF THE PREFERRED EMBODIMENTS

The suturing instrument of the present invention can be utilized to suture any type of anatomical tissue in any type of anatomical cavity; and, accordingly, while the instrument is described hereinafter for use with a portal sleeve in endoscopic procedures, such as laparoscopy, the instrument can be used in open surgery and with catheters and other small and large diameter tubular or hollow, cylindrical members providing access to small cavities, such as veins and arteries, as well as large cavities, such as the abdomen.

A suturing instrument 10 in accordance with the present invention, as illustrated in FIGS. 1–4, includes a handle 12, an outer tubular member 14 extending distally from the handle, an inner tubular member 16 disposed in the outer tubular member with a small radial clearance to define an annular space 18 therebetween, and a pair of needle holders 20 and 22 movably disposed in the annular space between the inner tubular member and the outer tubular member.

Figures 1, 2, 3, 4, 5:
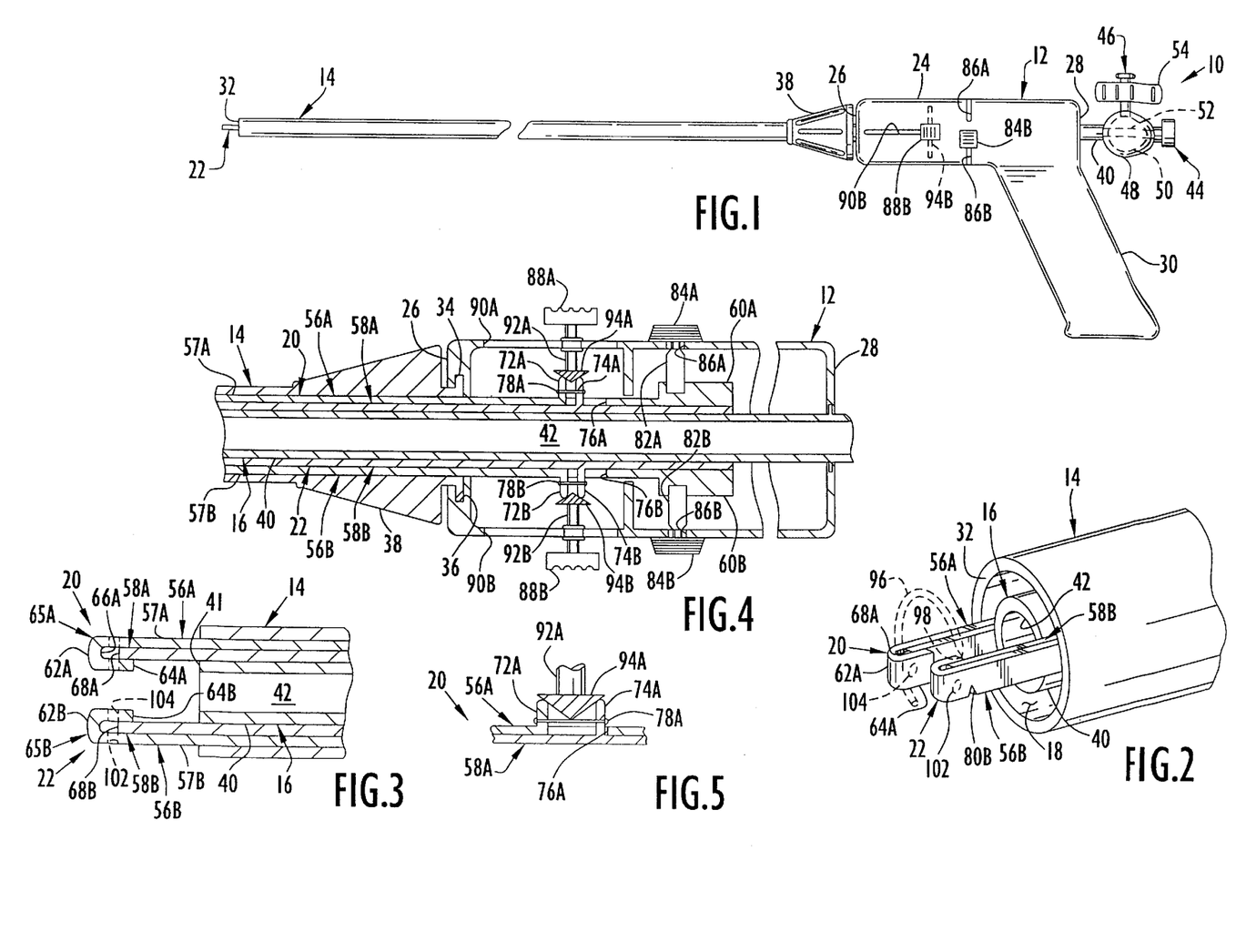
FIG. 1 is a side view, broken longitudinally, of a suturing instrument according to the present invention.
FIG. 2 is a fragmentary perspective view of the distal end of the suturing instrument of FIG. 1.
FIG. 3 is a fragmentary top view, partly in section, of the distal end of the suturing instrument of FIG. 1.
FIG. 4 is a fragmentary top view, partly in section, of the handle of the suturing instrument of FIG. 1.
FIG. 5 is an enlarged fragmentary top view, partly in section, illustrating operation of needle holding members of the needle driver.

Handle 12 includes a hollow cylindrical body or housing 24 with longitudinally spaced front and rear walls 26 and 28 oriented perpendicular to a longitudinal axis of the housing and a pistol grip 30 extending transversely from the housing at an acute angle relative to the proximal direction. The handle can be made of any substantially rigid medical grade material but is preferably formed of a plastic material of relatively high durometer to reduce weight while offering structural support for the distally extending members of the instrument.

Outer tubular member 14 is open at both ends and extends distally from handle 12 through an opening in front wall 26 of the handle housing. Distal end 32 of the outer tubular member can be blunt as shown, tapered, beveled, slotted or chamfered as desired or have any other suitable distal configuration. Preferably, outer tubular member 14 is made of a substantially cylindrical length of a substantially rigid material, such as stainless steel or some other medically acceptable plastic or metal material. The outer tubular member terminates proximally at an outwardly extending flange 34 rotatably received within an annular recess 36 formed in the front wall of the handle housing. A frusto-conical collar 38 of decreasing diameter in the distal direction extends outwardly from the outer tubular member adjacent the front wall of the handle housing and is configured with longitudinal fluting to facilitate manual rotation of one or more of the distally extending members of the instrument.

Inner tubular member 16 includes a hollow cylindrical portion 40 disposed coaxially within outer tubular member 14 and having an outer diameter somewhat smaller than the inner diameter of the outer tubular member to define an annular space 18 therebetween having a radius of curvature approximately equal to or commensurate with the radius of curvature of the suture needle to be used. The hollow cylindrical portion 40 of the inner tubular member extends from a distal end 41 aligned with distal end 32 of the outer tubular member through rear wall 28 of the handle housing to define a longitudinal operating channel or passage 42 through the instrument. The inner tubular member terminates at a coupling 44, for example, a Luer lock, for connection with sources of fluid or suction, operating units, medical instruments and accessories, with a valve 46 being disposed between the hollow cylindrical portion of the inner tubular member and coupling, the valve including a hollow spherical valve housing 48 preferably formed integrally with the inner tubular member from a substantially rigid medically acceptable plastic or metal material, and a spherical valve member 50 with a cylindrical aperture opening 52 formed therethrough rotatably disposed within the valve housing and connected with a knob 54.

Hereinafter, needle holder 20 will be referred to as a needle driver and needle holder 22 will be referred to as a needle catcher; it being understood that such designations are merely for purposes of clarity and that either needle holder can be used to drive a suture needle through anatomical tissue or to catch the end of the suture needle being driven in accordance with the present invention. Needle driver 20 and needle catcher 22 each include a pair of cooperating needle holding members mounted by the handle for rotation along arcuate paths within the annular space, the needle holding members further being movable relative to one another to selectively grasp and release a suture needle during suturing procedures.

As best seen in FIGS. 2 and 3, needle holding members 56a and 58a of needle driver 20 are each formed of a rigid, semi-rigid or flexible strip of medically acceptable material, such as stainless steel, with each of the strips having an appropriate thickness and width to permit sliding movement of the needle holding members relative to one another and the handle within the annular space. The outer needle holding member 56a includes an elongate portion or leg 57a extending distally from a generally rectangular fin-like appendage or plate 60a oriented radially within handle housing 24 to a bend 62a where the outer needle holding member folds inwardly upon itself to form a short leg 64a parallel to the elongate portion or leg of the needle holding member thereby defining a hook 65a having a mouth 66a with a gap width suitable for receiving the shaft or body of a suture needle. The inner needle holding member 58a is slidingly disposed between outer needle holding member 56a and inner tubular member 16 and includes a distal end 68a configured to fit within the mouth of the hook as a keeper, the distal end of the inner needle holding member preferably having a scalloped edge with one or more curved recesses (see, e.g., FIG. 17 at 370a) to fit conformally against and frictionally engage a suture needle held within the mouth of the hook with added security. A cut-out or tongue 72a extends radially outward from outer needle holding member 56a within the handle housing, and a similar cut-out or tongue 74a extends outwardly from inner needle holding member 58a through a slot 76a in the elongate portion or leg of the hooked needle holding member to be disposed adjacent the outer needle holding member tongue 72a. A bias member 78a, for example an elastic band or spring, is held in tension around tongues 72a and 74a to bias the tongues together so that the distal end 68a of the inner needle holding member is moved distally relative to the outer needle holding member to an extended position where the distal end of the inner needle holding member is disposed within mouth 66a of hook 65a and suitably spaced from bend 62a of the hook to securely grasp a suture needle disposed within the hook. Outer needle holding member 56a is also shown with a notch 80a of generally V-shaped configuration formed in the long leg of the hook opposite the short leg and configured with one or more sharp edges to cut lengths of suture material received therein under pressure.

The generally rectangular fin-like appendage or plate 60a at the proximal end of outer needle holding member 56a extends radially outward from the needle holding member parallel with a longitudinal axis of the needle holding member and is slidingly received within a slot formed at the bottom end of a post 82a. Post 82a is positioned to slidingly engage the fin-like appendage 60a at the proximal end of the outer needle holding member through the full range of longitudinal travel of the needle holding member and extends radially outward therefrom to connect with a knob 84a disposed outside the handle housing via a slot 86a formed part way (e.g., slightly less than about 180°) about the circumference of the cylindrical handle housing 24 perpendicular to the longitudinal axis of the housing. Knob 84a is movable along slot 86a to rotate needle driver 20 about the longitudinal axis of the instrument.

A push button 88a slides along a longitudinal slot 90a formed on one side of the handle housing and includes a plunger 92a with a wedge 94a of semi-circular configuration disposed at a terminal end, the wedge being of decreasing lateral dimension in a radially inward direction to spread tongues 72a and 74a of the outer and inner needle holding members 56a and 56b apart regardless of angular location when in a depressed position or condition, as shown in FIG. 5, and to be disposed in the longitudinal path of movement or travel of the tongues when in an elevated or nondepressed position or condition, as shown in FIG. 4, such that movement of the push button along the slot will cause the wedge to contact one of the tongues thereby imparting longitudinal movement to the needle driver. Push button 88a is preferably of a known type which will alternatingly extend and retract the plunger in response to repeated depression.

Needle holding members 56b and 58b of needle catcher 22 are shown as being identical to the needle holding members 56a and 58a of the needle driver; however, knob 84b at the proximal end of the needle catcher is slidably disposed within a circumferential slot 86b formed in handle housing 24 in laterally opposed relation to slot 86a, and pushbutton 88b is slidably disposed within a longitudinal slot 90b formed in the handle housing in laterally opposed relation to slot 90a. While needle driver 20 and needle catcher 22 are shown as being identical, it will be appreciated that the needle driver and the needle catcher can be of different configuration dependent upon procedural use and other considerations such as cost.

In use, instrument 10 is grasped using pistol grip 30 and, in the case of an endoscopic procedure, the instrument is guided to the operative site by a portal sleeve positioned in the wall of an anatomical cavity. The portal sleeve can be positioned in the anatomical cavity wall using any suitable penetrating technique, including those creating puncture sites by means of removable obturators, such as trocars, and can include a valve housing, if desired, to prevent loss of pneumoperitoneum during insertion and withdrawal of the instrument. Visualization of the endoscopic procedure can be accomplished using a conventional endoscope incorporated into the instrument, for example within the longitudinal operating channel 42 defined by tubular shaft 40, or separately positioned within the anatomical cavity through a second portal sleeve located at another puncture site.

Prior to insertion, instrument 10 is preferably in the position shown in FIGS. 3 and 4. More specifically, needle driver 20 and needle catcher 22 are preferably initially positioned at diametrically opposed locations within annular space 18, for example by sliding knobs 84a and 84b counterclockwise, looking proximally, until posts 82a and 82b abut respective terminal ends of circumferential slots 86a and 86b. In addition, push buttons 88a and 88b are preferably initially disposed at respective proximal ends of longitudinal slots 90a and 90b and in the elevated positions shown in FIG. 4 so that each of the needle holders will be in the closed or grasping position with distal ends 68a and 68b of the inner needle holding members or keepers 58a and 58b being disposed within hooks 65a and 65b at the distal end of the outer needle holding members 56a and 56b.

A curved suture needle 96 of substantially semi-circular configuration, shown by broken lines in FIG. 2, is positioned in needle driver 20 by moving the needle holding members 56a and 58a to the open position, placing the suture needle in the mouth of hook 65a, and moving the needle holding members to the closed position to hold the suture needle in place. Needle holding members 56a and 58a are moved to the open position by depressing the push button 88a to cause the wedge 94a to spread tongues 72a and 74a apart against the influence of bias member 78a, as shown in FIG. 5, such that distal end 68a of the inner needle holding member 58a is moved proximally relative to hook 65a. The proximal end of needle 96 is then placed in the mouth of the hook with the sharp, tissue penetrating tip 98 of the needle being circumferentially aligned with and spaced from hook 65b at the distal end of needle catcher 22. With needle 96 positioned within hook 64a of needle driver 20, push button 88a on the side of the instrument corresponding to the needle driver is depressed to cause the wedged-shaped terminal end 94a to elevate or move away from tongues 72a and 74a so that the tongues can move together under the influence of bias member 78a. Movement of tongue 72a towards tongue 74a causes distal end 68a of the inner needle holding member to move distally relative to hook 65a and into contact with the body of needle 96 as shown in FIG. 2. Needle 96 is thus held securely between inner and outer needle holding members 56a and 58a, which are operated remotely, and will thus move with needle driver 20 during the suturing procedure.

Prior to suturing, needle catcher 22 is configured to receive the tip of the suture needle by remotely moving needle holding members 56b and 58b to the open position prior to, during or after the suture needle has been loaded in needle driver 20. This is accomplished by depressing the push button 88b to cause the wedge 94b at the terminal or inner end of the plunger to spread tongues 72b and 74b apart against the influence of bias member 78b such that distal end 68b of the inner needle holding member 58b is moved proximally relative to hook 65b.

Figure 6:
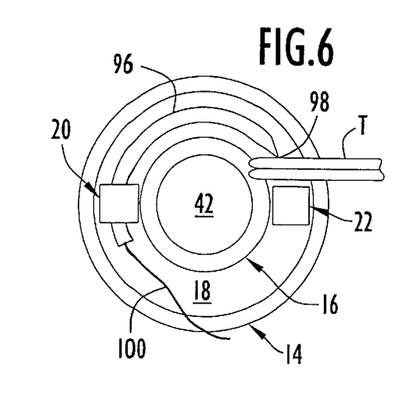
FIGS. 6–12 are front views of the suturing instrument of FIG. 1 illustrating use of the instrument for suturing anatomical tissue with a curved suture needle.
Figure 7:
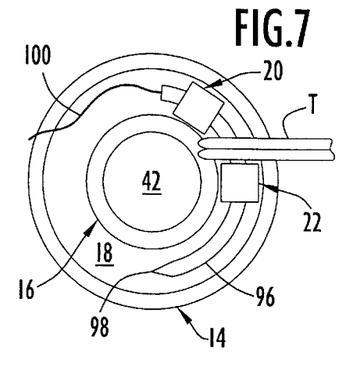

Referring now to FIG. 6, anatomical tissue T is positioned between tip 98 of needle 96 and the needle catcher 22 with a length of suture material 100 being shown attached to the proximal end of the needle for purposes of illustration only. Using the open needle catcher 22 as a backing or support for the tissue, the needle is driven through tissue T and into the needle catcher by rotating knob 84a in a clockwise direction, looking proximally, until post 82a abuts the opposite terminal end of slot 86a or needle driver 20 abuts the tissue being sutured. Tip 98 of needle 96 is thus caused to penetrate through the anatomical tissue T and needle catcher 22 along an arcuate path having a radius of curvature approximately equal to or commensurate with the radius of curvature of the needle until the tip is disposed at a location spaced clockwise from the needle catcher as shown in FIG. 7. During rotation of needle driver 20, it will be appreciated that tongues 72a and 74a at the proximal ends of needle holding members 56a and 56b will slide along the arcuate terminal portion 94a of push button 88a but will not spread apart, thus maintaining grasping pressure on the suture needle.

With needle 96 positioned in needle catcher 22, push button 88b on the side of the instrument corresponding to needle catcher 22 is depressed to cause the plunger to be retracted thereby permitting tongues 72b and 74b of the inner and outer needle holding members 56b and 58b of needle catcher 22 to move together under the influence of bias member 78b and causing distal end 68b of the inner needle holding member to contact the body of the suture needle to retain the needle between the hook 65b of the outer needle holding member and the distal end 68b of the inner needle holding member. Button 88a on the side of the instrument corresponding to needle driver 20 may then be depressed to extend the plunger and cause inner and outer tongues 74a and 72a to move apart, thereby moving the distal end 68a of the inner needle holding member proximally relative to hook 65a of the outer needle holding member.

Figures 8, 9:
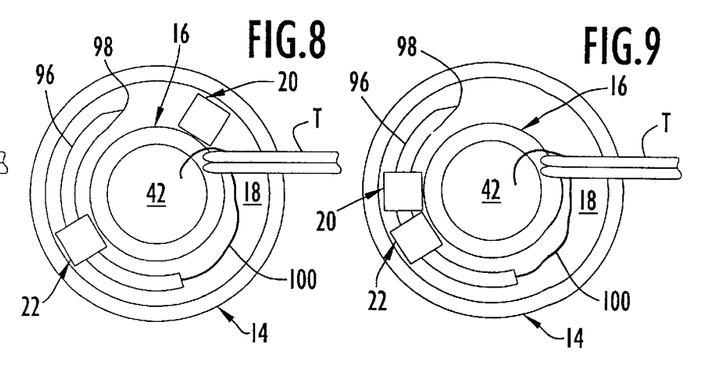

With needle 96 secured within needle catcher 22, knob 84b is rotated clockwise, looking at FIG. 8, until post 82b abuts a terminal end of circumferential slot 86b and the tip of needle 96 extends approximately 90° into the portion of the annular space in which the needle driver 20 is movable. Suture needle 96 is thus pulled through the anatomical tissue with the length of suture material 100. Needle driver knob 84a is then rotated in a counterclockwise direction about 180°, looking at FIG. 9, to receive the tip of suture needle 96. At this point, the needle driver push button 88a is depressed to elevate the plunger so that suture needle 96 is secured between the distal end 68a of inner needle holding member 58a and hook 65a at the distal end of outer needle holding member 56a. At about the same time, needle catcher push button 88b is depressed to cause the plunger to lower thereby releasing the suture needle from the needle catcher.

Figure 10:
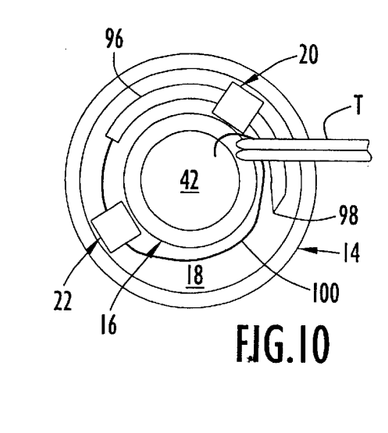
Figure 11:
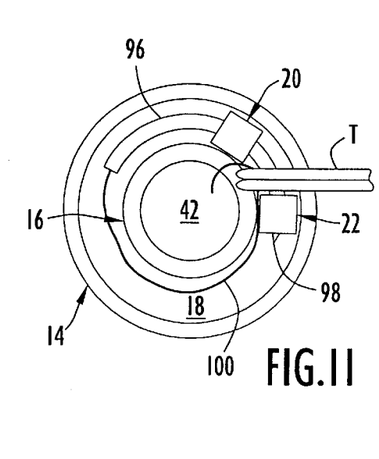
Figure 12:
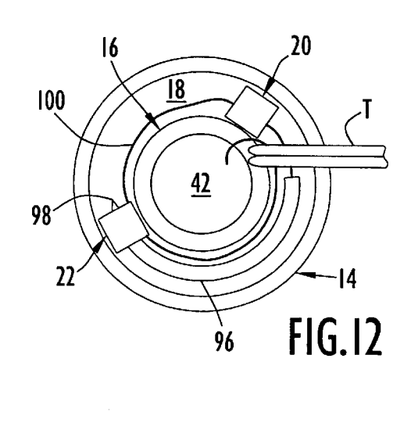

A second stitch can optionally be made by moving suturing instrument 10 slightly relative to tissue T and rotating needle driver rotation knob 84a clockwise, looking at FIG. 10, to cause tip 98 of suture needle 96 to penetrate through the tissue at a second location. Needle catcher 22 has preferably previously been rotated in a counterclockwise direction, looking at FIG. 11, by rotation of the needle catcher rotator knob 84b along slot 86b to receive the suture needle, after which needle catcher operating button 88b is elevated to secure suture needle 96 within the needle catcher. At about the same time, the needle driver operating button 88a is depressed to permit the suture needle to be pulled completely through the tissue by clockwise rotation of the needle catcher 22 as shown in FIG. 12. At this point, the suture needle 96 may have to be advanced circumferentially in the clockwise direction in order for the tip 98 to protrude sufficiently from the needle catcher for additional stitches to be formed. Such repositioning can, for example, be accomplished by grasping the proximal end of the needle with a separate needle holding instrument and releasing the needle holding members to allow manipulation of the needle to a position in the needle holder wherein the tip of the needle protrudes sufficiently to pass through the anatomical tissue and be captured by the needle driver.

At any point during the operative procedure, operating channel 42 of the suturing instrument can be used for irrigation or apsiration and can serve as a space for holding the suture material or as a portal for the introduction of other medical instruments such as, for example, forceps, cutting members and endoscopes.

Figures 17, 18:
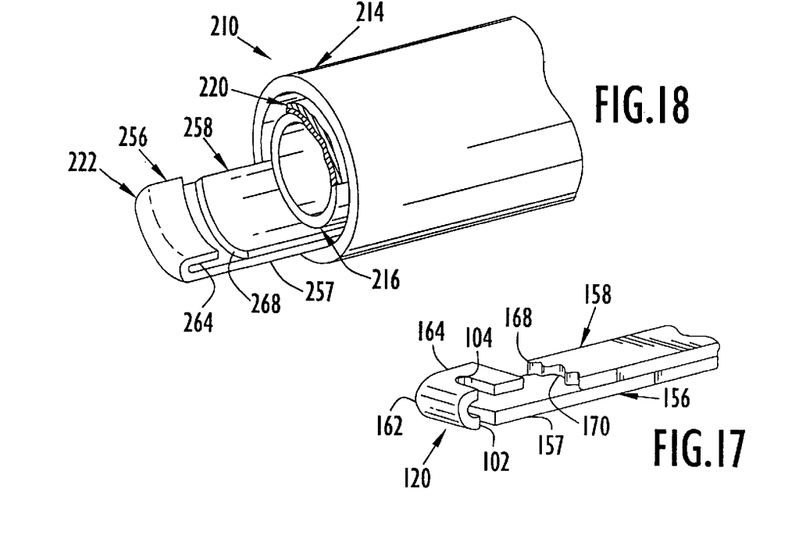
FIG. 17 is a fragmentary perspective view of a modification of the suturing instrument according to the present invention.
FIG. 18 is a fragmentary perspective view, partly broken, of another modification of the suturing instrument according to the present invention.

Needle holders 20 and 22 can be modified to suture anatomical tissue with straight or slightly curved suture needles by forming openings through long and short legs of the hooks 65a and 65b in opposed relation, for example as shown by broken lines at 102 and 104 in FIGS. 2 and 3, and biasing distal ends of the needle holders to bend away from one another at an angle relative to a longitudinal axis of the instrument. Openings 102 and 104 are shown as being of circular configuration with a diameter to receive a suture needle oriented substantially perpendicular to a longitudinal axis of the needle holder, but can be of slotted configuration as shown in FIG. 17 or have any other configuration to receive a suture needle.

Figure 13:
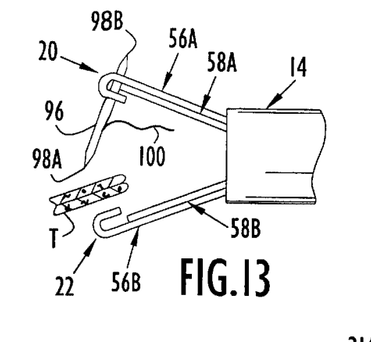
FIGS. 13–16 are fragmentary side views illustrating use of the suturing instrument of FIG. 1 to suture anatomical tissue with a straight needle.

Use of suturing instrument 10 to suture anatomical tissue T with a straight suture needle 96 is illustrated in FIGS. 13–16. Referring to FIG. 13, needle driver 20 and needle catcher 22 are moved to the open position shown by advancing push buttons 88a and 88b distally along slots 90a and 90b to cause the needle holders to protrude distally from outer tubular member 14. In the extended position, the needle driver 20 and needle catcher 22 are biased apart such that tissue T can be positioned in the space between the needle catcher and the tip of a suture needle held within the needle driver.

Referring still to FIG. 13, a suture needle 96 having sharp, tissue penetrating tips 98a and 98b at opposite axial ends is positioned within the needle driver 20 through openings 102 and 104 formed through the hook at the distal end of the outer needle holding member 56a. Inner needle holding member 58a is advanced distally relative to outer needle holding member 56a, for example by elevating the needle driver operating button 88a in the manner described above, to prevent the suture needle from moving relative to the needle driver during penetration of the anatomical tissue. For purposes of illustration, a length of suture material 100 is shown connected to a medial portion of the suture needle 96 and can, for example, be introduced at the operative site through the longitudinal operating channel 42 defined by inner tubular member 16.

Figure 14:
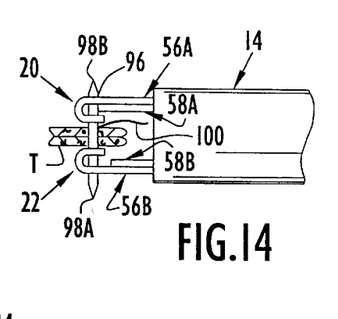
Figure 15:
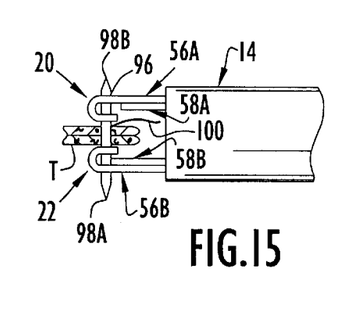
Figure 16:
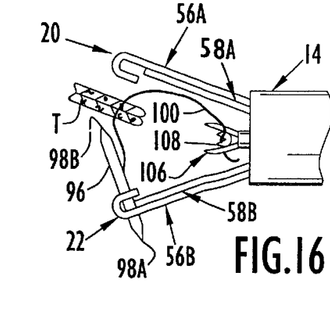

Tip 98a of suture needle 96 is caused to penetrate through anatomical tissue T by moving push buttons 88a and 88b proximally along slots 90a and 90b, respectively, to force the needle driver 20 to move towards the needle catcher 22 as shown in FIG. 14. Tip 98a emerges from the tissue T and passes through openings 102 and 104 in the needle catcher 22, after which the needle is secured in the needle catcher by advancing the inner needle holding member 58b distally and released from the needle driver 20 by retracting the inner needle holding member 58a proximally as shown in FIG. 15. The remainder of the suture needle 96 is pulled through the anatomical tissue T by moving the needle driver 20 and needle catcher 22 distally relative to outer tubular member 14 so as to permit the driver and catcher to move to the opened position shown in FIG. 16 whereby the needle is released from the needle driver and pulled through the anatomical tissue with the suture material 100 by the needle catcher. For purposes of illustration, a forceps 106 carrying a knotting element 108 is shown extending from longitudinal channel 42 defined by inner tubular member 16. If desired, such knotting elements can be used in lieu of traditional knotting techniques during the suturing procedure. Some examples of suitable knotting elements for this purpose are described in pending applications Ser. No. 08/366,285, filed Dec. 29, 1994; Ser. No. 08/377,723, filed Jan. 25, 1995; Ser. No. 08/401,002, filed Mar. 9, 1995; and Ser. No. 08/585,875, filed Jan. 16, 1996, the disclosures of which are incorporated herein by reference. In addition, since opposite axial ends of suture needle 96 are provided with sharp, tissue penetrating tips 98a and 98b, it is possible to penetrate the anatomical tissue T at multiple locations in order to form a continuous run of stitches merely by performing the above steps in reverse order.

FIG. 17 illustrates a modified needle holder 120 with longitudinally aligned openings 102 and 104 similar to those described above but of slotted configuration, the slotted openings extending transversely, relative to a longitudinal axis of the needle holder, from respective open ends disposed along a lateral or longitudinal edge of the outer needle holding member 156 to generally centrally located terminal ends of rounded or semicircular configuration with a size to receive a suture needle. The slotted openings permit positioning of a suture needle in the needle holder in the manner shown in FIGS. 13–16 without passing the tip of the needle through holes. Accordingly, the modified needle holder 120 prevents damage or dulling of the tip of the needle which could potentially complicate the suturing procedure. Scalloped edge 170 at the distal end 168 of inner needle holding member 158 is configured with laterally spaced recesses, one of which is preferably aligned with the terminal portion or end of the slotted openings to cradle a needle positioned within the openings in a manner to secure the needle during suturing procedures.

Another modification of the suturing instrument according to the present invention is shown in FIG. 18 wherein the modified suturing instrument 210 includes a pair of needle holders 220 (only a portion of which is shown for clarity)

and 222 similar to those described above but with wider needle holding members 256 and 258 curved across their width to provide additional support for the body of a curved suture needle while still being able to slide conformally within the annular space between inner and outer tubular members 216 and 214.

Figure 19:
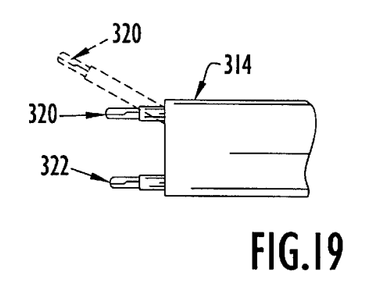
FIG. 19 is a fragmentary side view of the distal end of another modification of a suturing instrument according to the present invention.
Figure 20:
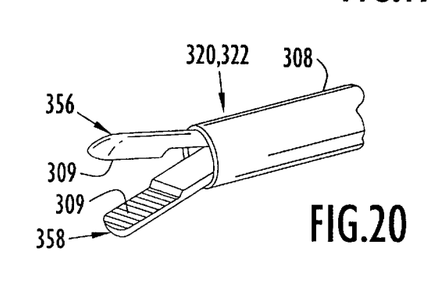
FIG. 20 is a fragmentary perspective view of the modified needle holding members of the suturing instrument shown in FIG. 19.

Yet another modification of the suturing instrument according to the present invention is shown in FIGS. 19 and 20 and involves modifying the needle holders to each include a pair of needle holding members 356 and 358 in the form of jaws which are preferably biased apart to an open position where at least one of the jaws extends at an angle relative to a longitudinal axis of the needle holder, the jaws being movable between the open position and a closed position by sliding a tubular member 308 proximally and distally relative to the jaws. If desired, tubular member 308 can be biased to move proximally or distally relative to the jaws 356 and 358 so that the jaws are normally in open or closed positions, respectively. The needle holding members or jaws 356 and 358 can be of integral one-piece design or can be formed separately and pivotally joined together, with each jaw being provided with cooperatively configured needle holding surfaces 309 of conventional design for holding a curved suture needle in a manner similar to that shown in FIGS. 6–12 when the jaws are moved toward one another to be in the closed position. It will be appreciated, however, that the jaws can also hold straight suture needles when rotated 90° about their respective longitudinal axes.

From the above, it will be appreciated that the suturing instrument according to the present invention permits suturing of anatomical tissue during endoscopic procedures without the need of having to use multiple needle holding instruments inserted through multiple puncture sites by inserting a needle driver and a needle catcher through a single puncture site with a suturing instrument having a handle operable to move the needle driver and the needle catcher relative to one another in a cooperative manner to suture the anatomical tissue. The needle driver and the needle catcher each include needle holding members selectively operable to grasp and release a suture needle so that, when the needle holding members of the driver are operated to grasp the suture needle, the driver can be moved in a direction to drive the suture needle through anatomical tissue positioned between the driver and the catcher, and when the needle holding members of the catcher are operated to grasp the suture needle, the needle holding members of the driver can be operated to release the suture needle, thereby allowing the catcher to be moved in a direction to pull the suture material through the anatomical tissue.

The needle driver and the needle catcher of the suturing instrument can be of the same design or of different designs so long as each includes a needle holder capable of grasping and releasing a needle. The needle holders can be configured to hold any type of needle including, but not limited to, straight and curved needles and are preferably mounted to permit movement of the needle holders relative to one another in directions causing the needles to be passed from one needle holder to the other. In the case of curved needles, the needle holders are preferably mounted for rotation about a longitudinal axis of the suturing instrument in an arcuate path having a radius of curvature commensurate with the radius of curvature of the needle. For straight needles, one or both of the needle holders is preferably pivotable away from a longitudinal axis of the suturing instrument and the needles are preferably held by the needle holders such that tissue penetrating tips of the needles are oriented toward the longitudinal axis of the instrument. One or more lengths of suture material can be attached to each suture needle at any desirable location along the body of tip of the needle including, but not limited to, the proximal end of the needle, intermediate or medial portions of the needle body, or locations adjacent the tip of the needle. It will also be appreciated that the suturing instrument according to the present invention can be used with any type of standard suturing needle including, but not limited to, needles having sharp or blunt tissue penetrating tips, and needles having tissue penetrating tips at opposite axial ends of a needle body.

The needle holding members of the needle catcher and the needle driver shown and described herein are exemplary of the types of needle holding members that can be used according to the present invention. Accordingly, the needle holding members can have any suitable configuration for cooperatively grasping needles to suture anatomical tissue including, but not limited to, configurations wherein the needle holding members pivot, slide or otherwise move relative to one another to capture and release a needle. The needle holding members can, for example, be of straight, curved or angled configuration and can provided with ribs, grooves, slots and/or holes along grasping surfaces to assure a positive grip. While the hooked needle holding member has been shown and described herein as being disposed radially outward of the straight needle holding member or keeper, it will be appreciated that the hooked member can be disposed radially inward of or circumferentially side-by-side with the keeper if desired. The needle holding members can also carry cutting members, such as slots with sharp edges or protruding blades, and can have opposed arcuate or concave portions for clamping tubular objects, such as organs, without compressing the objects.

The needle driver and catcher of the present invention are preferably movably disposed about a tubular member defining a central channel or passage through the instrument to permit various medical devices and instruments such as, for example, needles, blades, forceps, cauteries, endoscopes, illuminating devices and lengths of suture material to be introduced at the operative site without the need of having to remove the suturing instrument from the body. The tubular member defining the operating channel can have any configuration in transverse cross-section including, but not limited to, elliptical, polygonal and irregular cross-sectional configurations. Also, all or part of the inner surface of the tubular member can be electrically insulated to permit passage of electrosurgical instruments therethrough. The valve and coupling shown at the proximal end of the tubular member are merely exemplary of the types of conventional valves and conventional couplings that can be used.

The handle shown and described herein for mounting the needle driver and the needle catcher is exemplary of the types of handles that can be used; accordingly, the handle can have any configuration for mounting the needle holders including, but not limited to, configurations wherein the handle includes pivoted legs with finger loops, one fixed and one pivoted leg with finger loops, a pistol grip with one or more movable triggers, and/or resilient U-shaped members. Moreover, the handle can have any orientation relative to the longitudinal axis of the instrument including, for example, substantially transverse orientations wherein the handle extends transversely relative to the longitudinal axis of the instrument, substantially longitudinal orientations wherein the handle is oriented substantially parallel to or at a small angle relative to the longitudinal axis of the instrument, or rotatable configurations wherein the handle can be moved between transverse and longitudinal orientations as desired.

The mechanisms shown for remotely operating the needle holding members of the needle catcher and the needle driver and for moving the needle catcher and needle driver relative to one another are merely exemplary of the types of mechanisms that can be used to perform these functions. For example, in the case of slidable needle holding members, mechanisms including, but not limited to, push-buttons with wedge-shaped members for engaging flanges carried by each member, resilient U-shaped members with arms connected to each member, and triggers connected to the members via linkages or gears can be used to move the needle holding members relative to one another. In the case of pivoted needle holding members or jaws, mechanisms such as, for example, a tubular member movable relative to the jaws or linkages connecting one or both of the jaws with a trigger or the like at a proximal end of the instrument can be used move the needle holding member or jaws relative to one another. The needle holding members can be biased to a particular position, condition or state such as, for example, a closed state for grasping a suture needle, and can be provided with locking features to permit the user to maintain the members in a desired position. "Remote operation" as used herein refers to selective operation of the needle holding members through any type of proximal controls.

Moving the needle driver and the needle catcher of the present invention relative to one another can be accomplished in any suitable manner, for example by connecting a knob at the proximal end of each needle holding instrument and sliding the knobs along slots formed in the handle housing or by mounting the needle holding instruments on geared components and moving the gears with a trigger or some other device. The particular length and curvature of the suture needles shown and described herein as well as any angular displacements of the needle driver and catcher shown and described herein are merely exemplary, and it will be appreciated that other needle lengths and angular displacements can be used.

The components of the suturing instrument of the present invention can be made of any suitable, medical grade materials to permit sterilization for reuse or disposal for single patient use. The components can be made of multiple parts of various configurations and materials to reduce cost. The handle housing can have various valves, stop cocks and seals therein to control the flow of fluid and medical devices through the suturing instrument.

The features of the various embodiments described above can be combined in any manner desired dependent upon the operational requirements of the procedure to be performed and the complexity of the suturing instrument. It will also be appreciated that the suturing instrument of the present invention can be used to apply single or multiple stitches in open or endoscopic procedures.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An instrument for suturing anatomical tissue with a suture needle, said suturing instrument comprising
   a handle;
   an elongate tubular member connected to and extending distally from said handle along a longitudinal axis;
   a needle driver disposed in said tubular member and mounted by said handle for rotation about said longitudinal axis along a first arcuate path; and
   a needle catcher disposed in said tubular member and mounted by said handle for rotation about said longitudinal axis along a second arcuate path coplanar with said first arcuate path;
   said needle driver and said needle catcher each including needle holding members operable to grasp and release the suture needle so that, when said needle holding members of said needle driver are operated to grasp the suture needle, said needle driver can be rotated to drive the suture needle through anatomical tissue positioned between said needle driver and said needle catcher, and when said needle holding members of said needle catcher are operated to grasp the suture needle, said needle holding members of said needle driver can be operated to release the suture needle, thereby allowing said catcher to be rotated to pull the suture material through the anatomical tissue.

2. A suturing instrument as recited in claim 1 wherein the first arcuate path and the second arcuate path each have a radius of curvature substantially commensurate with a radius of curvature of the suture needle.

3. A suturing instrument as recited in claim 1 wherein said elongate tubular member has a proximal end mounted by said handle and a distal end, wherein proximal ends of said needle driver and said needle catcher are mounted by said handle and distal ends of said needle driver and said needle catcher protrude from said distal end of said elongate tubular member.

4. A suturing instrument as recited in claim 3 wherein respective distal ends of said needle driver and said needle catcher are longitudinally movable relative to said elongate tubular member between extended positions where said needle driver and said needle catcher bend outwardly away from said longitudinal axis of said elongate tubular member and retracted positions where said needle driver and said needle catcher are forced inwardly toward said longitudinal axis.

5. A suturing instrument as recited in claim 4 wherein each of said needle driver and said needle catcher includes a first needle holding member having a distal end in the form of a hook and a second needle holding member having a distal end movable relative to said hook to grasp and release suture needles disposed within said hook, wherein openings are formed through opposing sides of said hook to receive the suture needle at an angle relative to a longitudinal axis of said first needle holding member.

6. A suturing instrument as recited in claim 5 wherein said openings are of circular configuration.

7. A suturing instrument as recited in claim 5 wherein said openings are of slotted configuration.

8. A suturing instrument as recited in claim 3 and further comprising an inner tubular member disposed within said elongate tubular member with a small radial clearance to define an annular space therebetween, said needle driver and said needle catcher being movably disposed within said annular space.

9. A suturing instrument as recited in claim 8 wherein said inner tubular member extends through said handle to define a longitudinal channel along the length of said instrument, and further comprising a coupling at a proximal end of said inner tubular member.

10. A suturing instrument as recited in claim 8 wherein said inner tubular member extends through said handle to define a longitudinal channel along the length of said instrument, and further comprising a valve disposed along said longitudinal channel to control passage of fluids and instruments therethrough.

11. A suturing instrument as recited in claim 1 wherein said needle driver and said needle catcher each include a first needle holding member having a distal end in the form of a hook and second needle holding member having a distal end movable in said hook to grasp and release a suture needle disposed therein.

12. A suturing instrument as recited in claim 11 wherein said distal end of said second needle holding member includes a recess for engaging a suture needle disposed within said hook.

13. A suturing instrument as recited in claim 5 wherein said distal end of said second needle holding member includes a recess aligned with said openings to engage a suture needle disposed within said openings.

14. A suturing instrument as recited in claim 11 and further comprising a notch formed in at least one of said first and second needle holding members for severing a length of suture material.

15. A suturing instrument as recited in claim 1 wherein said needle driver and said needle catcher each include a pair of opposed jaw members with cooperative needle holding surfaces and means operable to open and close the jaw members.

16. A suturing instrument as recited in claim 1 wherein said needle driver and said needle catcher are each remotely operable.

17. A suturing instrument as recited in claim 1 wherein said needle driver and needle catcher are rotated in one of a first plane disposed substantially perpendicularly to the longitudinal axis and a second plane disposed coextensively with the longitudinal axis when the needle driver drives the suture needle through the anatomical tissue and the needle catcher pulls the needle through the anatomical tissue.

18. A method of suturing anatomical tissue using a length of suture material attached to a curved suture needle, said method comprising the steps of providing a suturing instrument having an elongate tubular member extending along a longitudinal axis with a needle driver and a needle catcher disposed in the tubular member and operative to rotate within the tubular member offset from and about the longitudinal axis;

grasping the suture needle with the needle driver mounted by a handle by remotely operating a needle holding member of the needle driver;

positioning the anatomical tissue between a tip of the suture needle and the needle catcher mounted by the handle;

rotating the needle driver in a first direction along an arcuate path to cause the tip of the needle to penetrate the anatomical tissue;

receiving the tip of the suture needle in the needle catcher;

grasping the suture needle with the needle catcher;

releasing the suture needle from the needle driver; and rotating the needle catcher in the first direction along a second arcuate path.

19. A method of suturing anatomical tissue as recited in claim 18 wherein the first arcuate path and the second arcuate path each have a radius of curvature commensurate with the radius of curvature of the suture needle.

20. A method of suturing anatomical tissue as recited in claim 19 wherein said grasping and release steps comprise remotely operating a needle holding member.

21. A method of suturing anatomical tissue using a length of suture material attached to a curved suture needle, said method comprising the steps of grasping the suture needle with a needle driver mounted by a handle by remotely operating a needle holding member of the needle driver;

positioning the anatomical tissue between a tip of the suture needle and a needle catcher mounted by the handle;

rotating the needle driver in a first direction along an arcuate path to cause the tip of the needle to penetrate the anatomical tissue;

receiving the tip of the suture needle in the needle catcher;

grasping the suture needle with the needle catcher;

releasing the suture needle from the needle driver;

rotating the needle driver in a second direction opposite the first direction to receive the tip of the suture needle held by the needle catcher;

grasping the suture needle with the needle driver;

releasing the suture needle from the needle catcher;

rotating the needle driver in the first direction to cause the tip of the suture needle to penetrate through the anatomical tissue; and rotating the needle catcher in the first direction along a second arcuate path.

* * * * *